United States Patent
Le Neel et al.

(10) Patent No.: US 10,429,330 B2
(45) Date of Patent: Oct. 1, 2019

(54) GAS ANALYZER THAT DETECTS GASES, HUMIDITY, AND TEMPERATURE

(71) Applicant: STMicroelectronics Pte Ltd, Singapore (SG)

(72) Inventors: Olivier Le Neel, Singapore (SG); Ravi Shankar, Singapore (SG); Shian Yeu Kam, Singapore (SG); Tien Choy Loh, Singapore (SG)

(73) Assignee: STMicroelectronics Pte Ltd, Singapore (SG)

( * ) Notice: Subject to any disclaimer, the term of this patent is extended or adjusted under 35 U.S.C. 154(b) by 62 days.

(21) Appl. No.: 15/213,230

(22) Filed: Jul. 18, 2016

(65) Prior Publication Data

US 2018/0017513 A1 Jan. 18, 2018

(51) Int. Cl.
*G01N 27/12* (2006.01)
*G01N 33/00* (2006.01)

(52) U.S. Cl.
CPC ....... *G01N 27/128* (2013.01); *G01N 33/0047* (2013.01)

(58) Field of Classification Search
CPC .................................................. G01N 27/121
(Continued)

(56) References Cited

U.S. PATENT DOCUMENTS 4,608,232 A 8/1986 Sunano et al.
4,938,053 A 7/1990 Jepson et al.
(Continued)

FOREIGN PATENT DOCUMENTS

CN 1961209 A 5/2007
CN 201307027 Y 9/2009
(Continued)

OTHER PUBLICATIONS

Allen et al., "Associations of Cognitive Function Scores with Carbon Dioxide, Ventilation, and Volatile Organic Compound Exposures in Office Workers: A Controlled Exposure Study of Green and Conventional Office Environments," *Environmental Health Perspective (Online)* 124(6):805, Jun. 2016. (33 pages).
(Continued)

*Primary Examiner* — Walter L Lindsay, Jr.
*Assistant Examiner* — Philipmarcus T Fadul
(74) *Attorney, Agent, or Firm* — Seed IP Law Group LLP

(57) ABSTRACT

A miniature gas analyzer capable of detecting VOC gases in ambient air as well as sensing relative humidity and ambient temperature can be used to monitor indoor air quality. The VOC gas sensor is thermally controlled and can be tuned to detect a certain gas by programming an adjacent heater. An insulating air pocket formed below the sensor helps to maintain the VOC gas sensor at a desired temperature. A local temperature sensor may be integrated with each gas sensor to provide feedback control. The heater, local temperature sensor, gas sensor(s), relative humidity sensor, and ambient temperature sensor are in the form of patternable thin films integrated on a single microchip, e.g., an ASIC. The device can be incorporated into computer workstations, smart phones, clothing, or other wearable accessories to function as a personal air quality monitor that is smaller, more accurate, and less expensive than existing air quality sensors.

20 Claims, 13 Drawing Sheets

(58) Field of Classification Search
USPC ........................................................ 73/25.05
See application file for complete search history.

(56) References Cited

U.S. PATENT DOCUMENTS

| | | |
|---|---|---|
| 5,834,777 A | 11/1998 | Wong |
| 6,111,280 A | 8/2000 | Gardner et al. |
| 6,243,474 B1 | 6/2001 | Tai et al. |
| 6,322,247 B1 | 11/2001 | Bonne et al. |
| 6,352,874 B1 | 3/2002 | McNeil et al. |
| 6,361,206 B1 | 3/2002 | Bonne |
| 6,383,832 B1 | 5/2002 | Nakabayashi |
| 6,478,974 B1 | 11/2002 | Lebouitz et al. |
| 6,546,812 B2 | 4/2003 | Lewis |
| 6,592,823 B1 | 7/2003 | Odermatt et al. |
| 6,698,297 B2 | 3/2004 | Gysling |
| 6,879,089 B2 | 4/2005 | Wong et al. |
| 7,280,436 B2 | 10/2007 | Pedersen |
| 7,437,951 B2 | 10/2008 | McDonald et al. |
| 7,556,895 B2 | 7/2009 | Moriya et al. |
| 7,703,339 B2 | 4/2010 | Sulouff, Jr. et al. |
| 7,821,085 B2 | 10/2010 | Suzuki et al. |
| 7,864,403 B2 | 1/2011 | Bita et al. |
| 7,946,505 B2 | 5/2011 | Lynam et al. |
| 8,062,497 B2 | 11/2011 | Witvrouw et al. |
| 8,304,850 B2 | 11/2012 | Lazarov et al. |
| 8,390,121 B2 | 3/2013 | Okumura et al. |
| 8,487,387 B2 | 7/2013 | Lin et al. |
| 8,696,989 B2 | 4/2014 | Esfandyarpour et al. |
| 8,715,514 B2 | 5/2014 | Lee et al. |
| 8,779,781 B2 | 7/2014 | Nguyen et al. |
| 8,806,933 B2 | 8/2014 | Kohno et al. |
| 8,852,513 B1 | 10/2014 | Speer et al. |
| 8,853,798 B2 | 10/2014 | Merz |
| 8,896,073 B2 | 11/2014 | Ponomarev et al. |
| 9,105,479 B2 | 8/2015 | Besling et al. |
| 9,164,052 B1 | 10/2015 | Speer et al. |
| 9,372,166 B2 | 6/2016 | Daamen et al. |
| 9,448,216 B2 | 9/2016 | Jin et al. |
| 9,459,224 B1 | 10/2016 | Cheng et al. |
| 2002/0160611 A1 | 10/2002 | Horsley |
| 2002/0166376 A1 | 11/2002 | Kohmura et al. |
| 2003/0039299 A1* | 2/2003 | Horovitz ............... G01N 27/123 374/141 |
| 2003/0079542 A1 | 5/2003 | Bonne et al. |
| 2004/0008041 A1* | 1/2004 | Davis ....................... G01D 5/24 324/664 |
| 2005/0109081 A1 | 5/2005 | Zribi et al. |
| 2005/0218465 A1* | 10/2005 | Cummins ............ G01N 27/121 257/414 |
| 2006/0162466 A1 | 7/2006 | Wargo et al. |
| 2008/0163687 A1 | 7/2008 | Kranz et al. |
| 2008/0194053 A1 | 8/2008 | Huang |
| 2008/0308920 A1 | 12/2008 | Wan |
| 2008/0315332 A1 | 12/2008 | Kaelberer et al. |
| 2009/0218702 A1 | 9/2009 | Beyne et al. |
| 2009/0243003 A1* | 10/2009 | Renna ................ B81C 1/00158 257/414 |
| 2010/0173437 A1 | 7/2010 | Wygant et al. |
| 2010/0314740 A1 | 12/2010 | Choi et al. |
| 2011/0031565 A1 | 2/2011 | Marx et al. |
| 2011/0045639 A1 | 2/2011 | Masuko et al. |
| 2011/0108932 A1 | 5/2011 | Benzel et al. |
| 2011/0150261 A1 | 6/2011 | Ho et al. |
| 2011/0298134 A1 | 12/2011 | Williams et al. |
| 2012/0024054 A1 | 2/2012 | Huang et al. |
| 2012/0032283 A1 | 2/2012 | Frey et al. |
| 2012/0144921 A1 | 6/2012 | Bradley et al. |
| 2012/0167392 A1 | 7/2012 | Cherian et al. |
| 2012/0168882 A1* | 7/2012 | Cherian ............ G01N 33/48785 257/414 |
| 2012/0171713 A1 | 7/2012 | Cherian et al. |
| 2012/0171774 A1 | 7/2012 | Cherian et al. |
| 2012/0299127 A1 | 11/2012 | Fujii et al. |
| 2012/0304742 A1* | 12/2012 | Cummins ............ G01N 27/121 73/31.06 |
| 2013/0010826 A1 | 1/2013 | Le Neel et al. |
| 2013/0036806 A1 | 2/2013 | Kohno |
| 2013/0106813 A1 | 5/2013 | Hotelling et al. |
| 2013/0139587 A1 | 6/2013 | Le Neel et al. |
| 2013/0202489 A1* | 8/2013 | Ong ..................... G01N 27/127 422/83 |
| 2013/0334620 A1 | 12/2013 | Chu et al. |
| 2013/0344609 A1 | 12/2013 | Mayer et al. |
| 2014/0197500 A1 | 7/2014 | Guillemet et al. |
| 2014/0264655 A1 | 9/2014 | Williams et al. |
| 2014/0264744 A1 | 9/2014 | Chu et al. |
| 2014/0268523 A1 | 9/2014 | Gogoi |
| 2014/0291677 A1 | 10/2014 | Le Neel et al. |
| 2014/0291829 A1 | 10/2014 | Le Neel et al. |
| 2014/0292317 A1 | 10/2014 | Le Neel et al. |
| 2014/0294046 A1 | 10/2014 | Le Neel et al. |
| 2014/0311905 A1 | 10/2014 | Stetter et al. |
| 2014/0353773 A1 | 12/2014 | Loh et al. |
| 2015/0323510 A1* | 11/2015 | Huynh ................. H01L 23/3157 73/23.34 |
| 2016/0018356 A1 | 1/2016 | Shankar et al. |
| 2017/0016866 A1* | 1/2017 | Chey ................. G01N 33/0027 |
| 2017/0066646 A1 | 3/2017 | Cheng et al. |
| 2017/0336343 A1* | 11/2017 | Bhat .................. G01N 27/4065 |
| 2017/0370865 A1* | 12/2017 | Samarao ............. G01N 27/125 |
| 2018/0017536 A1 | 1/2018 | Le Neel et al. |

FOREIGN PATENT DOCUMENTS

| | | |
|---|---|---|
| CN | 201589950 U | 9/2010 |
| CN | 101975751 A | 2/2011 |
| CN | 102680016 A | 9/2012 |
| CN | 102680018 A | 9/2012 |
| CN | 102735716 A | 10/2012 |
| CN | 101788315 B | 11/2012 |
| CN | 102879648 A | 1/2013 |
| CN | 102915993 A | 2/2013 |
| CN | 202770456 U | 3/2013 |
| CN | 103226040 A | 7/2013 |
| CN | 103512926 A | 1/2014 |
| CN | 103528620 A | 1/2014 |
| CN | 103728350 A | 4/2014 |
| CN | 105510526 A | 4/2016 |
| JP | 58-106451 A | 6/1983 |
| JP | 4-164242 A | 6/1992 |
| TW | 200531224 A | 9/2005 |
| WO | 2005/087471 A1 | 9/2005 |
| WO | 2015/071337 A1 | 5/2015 |

OTHER PUBLICATIONS

World Health Organization, "7 million premature deaths annually linked to air pollution," News Release, Mar. 25, 2014, retrieved from http://www.who.int/mediacentre/news/releases/2014/air-pollution/en/ on Jul. 5, 2016, 4 pages.

Lim et al., "The humidity effect on air flow rates in a critical flow venturi nozzle," Flow Measurement and Instrumentation 22(5):402-405, 2011.

Wilson et al., APTI Course 435 Atmospheric Sampling: Student Manual, United States Environmental Protection Agency, Research Triangle Park, North Carolina, USA, Sep. 1980, Chapter 3, "Air measuring instruments," pp. 3-1 to 3-49. (61 pages).

* cited by examiner

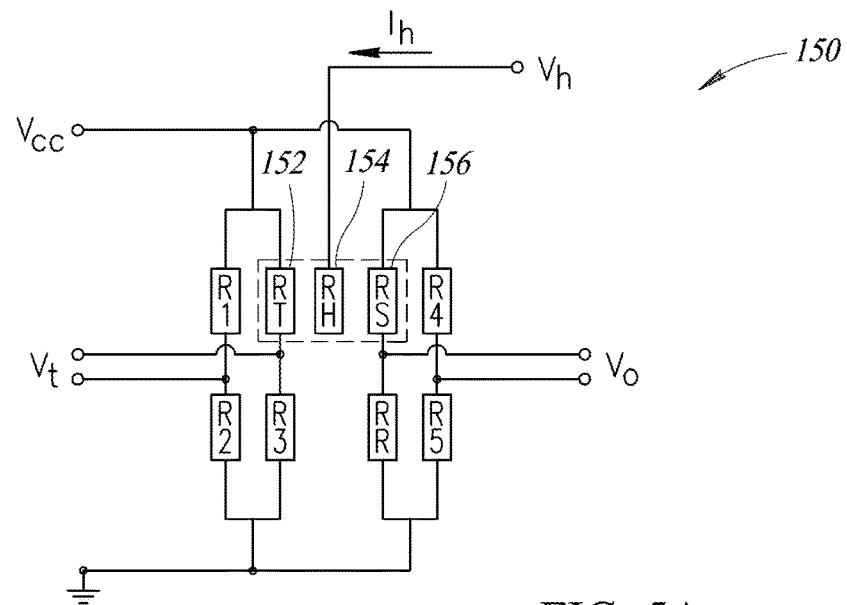
FIG. 5A
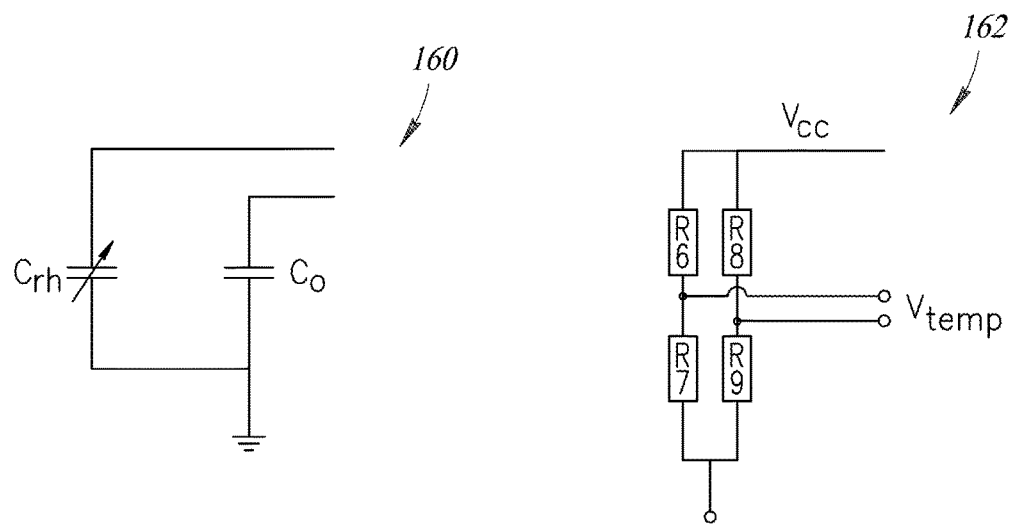
FIG. 5B
FIG. 5C

GAS ANALYZER THAT DETECTS GASES, HUMIDITY, AND TEMPERATURE

BACKGROUND

Technical Field

The present disclosure relates to miniature sensors for use in monitoring indoor air quality to detect gas phase molecules such as carbon dioxide and volatile organic compounds.

Description of the Related Art

It is believed that as many as seven million premature deaths occur annually due to air pollution [*World Health Organization Report*, Mar. 25, 2014]. Air pollution includes both outdoor pollution and poor indoor air quality in enclosed spaces such as, for example, homes, factories, office buildings, and high-density apartment buildings. Indoor air pollution is considered by some experts to be a larger health hazard than outdoor air pollution. Many of the illnesses and deaths associated with indoor air pollution are attributable to the use of solid fuels for heating and cooking in third world countries. However, industrial societies using cleaner forms of energy continue to suffer health effects from indoor pollution. In a typical day, each office worker inhales and processes about fifteen cubic meters of air, exhaling about 350 liters of carbon dioxide ($CO_2$). High levels of volatile organic compounds (VOCs) exist in many buildings constructed using engineered materials that contain glues, dyes, binding agents, adhesives, and the like. Furthermore, cleaning products, solvents, paint and other coatings, furniture, carpeting, and other indoor chemical sources also contribute VOC pollutants. VOCs include such compounds as ethanol, toluene, benzene, formaldehyde, trichloroethylene (TCE), and methylene chloride.

As heat efficiency of buildings improves and structures have become more airtight, there is less air circulation and a reduction in the exchange of air from outside to inside. As stale air accumulates within a closed space, concentrations of carbon dioxide and VOCs may rise to harmful levels. In some cases, cardio-pulmonary function may be compromised, increasing the risk of heart attacks and strokes. With continued exposure to poor air quality, over time, cancer may be triggered by such airborne toxins. Furthermore, a subtler and more common consequence of poor air quality is that the brain becomes deprived of oxygen, and productivity is reduced. A Harvard study funded by the National Institutes of Health (NIH) shows that a typical indoor $CO_2$ level of about 950 ppm impairs cognitive ability, ultimately lowering worker productivity. [J. G. Allen et al., "Associations of Cognitive Function Scores with Carbon Dioxide, Ventilation, and Volatile Organic Compound Exposures in Office Workers: A Controlled Exposure Study of Green and Conventional Office Environments," Environmental Health Perspectives, DOI:10.1289/ehp.1510037, Oct. 26, 2015]. Consequently, green building practices have been introduced in an attempt to limit the use of VOCs and, in some cases, to require a higher outdoor air ventilation rate to prevent accumulation of both VOCs and $CO_2$.

Maintaining awareness of the levels of VOCs and $CO_2$ present in indoor air is challenging. While some people are particularly sensitive to VOCs and will experience allergic reactions such as headaches, dizziness, and irritation of the eyes, nose, and throat in a high-VOC environment, most people cannot detect hazardous levels of pollution. Because VOCs and $CO_2$ are both odorless, they are generally difficult to detect, and most buildings today are not equipped with multi-species gas sensors. Some portable air quality alert devices that contain $CO_2$ and VOC sensors are available, e.g., AirVisual Node™, Alima™, Atmotube™, Cube Sensor™, and the like, however, such devices tend to be bulky and each unit that is capable of monitoring a personal sphere of exposure costs hundreds of dollars.

BRIEF SUMMARY

A gas analyzer implemented as a micro-sensor device detects VOCs in ambient air to monitor indoor air quality. The gas analyzer also includes temperature and humidity sensors formed on the same integrated circuit chip as the VOC sensor, providing secondary information to calibrate the VOC sensor. The VOC detector is a solid state, semiconductor-metal-oxide (SMO)-based sensor formed on a semiconductor substrate, as described in a U.S. patent application Ser. No. 15/213,100 issued as U.S Pat. No. 10,254, 261 by the present inventors, entitled "Integrated Air Quality Sensor" (hereinafter "LeNeel") . A multi-species gas sensor chip that is configured to detect different gases can be incorporated into indoor fixtures such as desktop computers or displays to monitor an individual's work environment. In addition, an integrated sensor chip can be incorporated into mobile devices such as laptop computers, smart phones, clothing, watches, and other accessories to function as a personal air quality monitoring device. Such a monitor can continuously measure an air quality index that includes VOC levels or levels of other gases detectable using a solid state SMO-based material.

A multi-species micro-sensor device detects multiple gas constituents in ambient air to monitor indoor air quality. In particular, three or more gas species detectors may be formed on a single integrated circuit chip, e.g., an application-specific integrated circuit (ASIC) that includes a volatile organic compound (VOC) sensor and a $CO_2$ sensor. The ASIC may also include other types of environmental sensors, as well as a processor and a memory.

Such a miniature multi-species sensor chip can be seamlessly and invisibly integrated into many different products. For example, a multi-species gas sensor chip can be incorporated into indoor fixtures such as desktop computers or displays to monitor an individual's work environment. In addition, an integrated sensor chip can be incorporated into mobile devices such as laptop computers, smart phones, clothing, watches, and other accessories to function as a personal monitoring device for air quality. Such an integrated multi-species gas sensor can continuously monitor an air quality index that includes levels of various gas species along with humidity, temperature, and the like.

An integrated multi-species gas micro-sensor is smaller, more accurate, and less expensive than existing air quality sensors. The multi-species gas micro-sensor includes a VOC sensor in the form of a conformal thin film less than 0.2 micron thick. The multi-species gas micro-sensor also includes a heater having a low temperature coefficient of resistance.

BRIEF DESCRIPTION OF THE SEVERAL VIEWS OF THE DRAWINGS

In the drawings, identical reference numbers identify similar elements or acts unless the context indicates otherwise. The sizes and relative positions of elements in the drawings are not necessarily drawn to scale.

FIGS. 5A, 5B, and 5C are circuit schematics of a VOC sensor, a relative humidity sensor, and an ambient temperature sensor, respectively, according to an embodiment as described herein.

DETAILED DESCRIPTION

Figure 1:
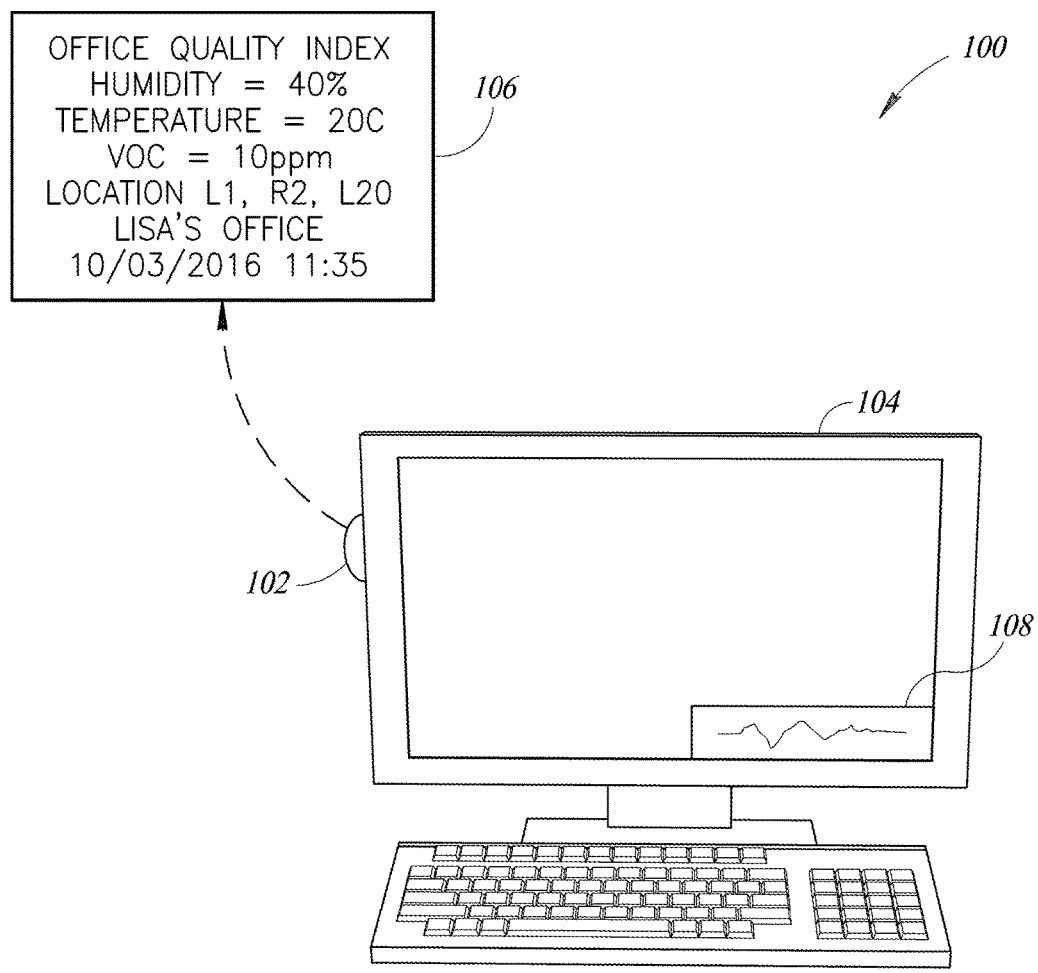
FIG. 1 is a pictorial view of a microelectronic gas analyzer in use, according to an embodiment as described herein.

In the following description, certain specific details are set forth in order to provide a thorough understanding of various aspects of the disclosed subject matter. However, the disclosed subject matter may be practiced without these specific details. In some instances, well-known structures and methods comprising embodiments of the subject matter disclosed herein have not been described in detail to avoid obscuring the descriptions of other aspects of the present disclosure.

Unless the context requires otherwise, throughout the specification and claims that follow, the word "comprise" and variations thereof, such as "comprises" and "comprising," are to be construed in an open, inclusive sense, that is, as "including, but not limited to."

Reference throughout the specification to "one embodiment" or "an embodiment" means that a particular feature, structure, or characteristic described in connection with the embodiment is included in at least one embodiment. Thus, the appearance of the phrases "In an embodiment" or "in an embodiment" in various places throughout the specification are not necessarily all referring to the same aspect. Furthermore, the particular features, structures, or characteristics may be combined in any suitable manner in one or more aspects of the present disclosure.

Reference throughout the specification to integrated circuits is generally intended to include integrated circuit components built on semiconducting substrates, whether or not the components are coupled together into a circuit or able to be interconnected. Throughout the specification, the term "layer" is used in its broadest sense to include a thin film, a cap, or the like and one layer may be composed of multiple sub-layers.

Reference throughout the specification to conventional thin film deposition techniques for depositing silicon nitride, silicon dioxide, metals, or similar materials include such processes as chemical vapor deposition (CVD), low-pressure chemical vapor deposition (LPCVD), metal organic chemical vapor deposition (MOCVD), plasma-enhanced chemical vapor deposition (PECVD), plasma vapor deposition (PVD), atomic layer deposition (ALD), molecular beam epitaxy (MBE), electroplating, electro-less plating, and the like. Specific embodiments are described herein with reference to examples of such processes. However, the present disclosure and the reference to certain deposition techniques should not be limited to those described. For example, in some circumstances, a description that references CVD may alternatively be done using PVD, or a description that specifies electroplating may alternatively be accomplished using electro-less plating. Furthermore, reference to conventional techniques of thin film formation may include growing a film in-situ. For example, in some embodiments, controlled growth of an oxide to a desired thickness can be achieved by exposing a silicon surface to oxygen gas or to moisture in a heated chamber.

Reference throughout the specification to conventional photolithography techniques, known in the art of semiconductor fabrication for patterning various thin films, includes a spin-expose-develop process sequence typically followed by an etch process. Alternatively or additionally, photoresist can also be used to pattern a hard mask (e.g., a silicon nitride hard mask), which, in turn, can be used to pattern an underlying film.

Reference throughout the specification to conventional etching techniques known in the art of semiconductor fabrication for selective removal of polysilicon, silicon nitride, silicon dioxide, metals, photoresist, polyimide, or similar materials includes such processes as wet chemical etching, reactive ion (plasma) etching (RIE), washing, wet cleaning, pre-cleaning, spray cleaning, chemical-mechanical planarization (CMP) and the like. Specific embodiments are described herein with reference to examples of such processes. However, the present disclosure and the reference to certain deposition techniques should not be limited to those described. In some instances, two such techniques may be interchangeable. For example, stripping photoresist may entail immersing a sample in a wet chemical bath or, alternatively, spraying wet chemicals directly onto the sample.

Specific embodiments are described herein with reference to miniature gas analyzers that have been produced; however, the present disclosure and the reference to certain materials, dimensions, and the details and ordering of processing steps are exemplary and should not be limited to those shown.

Turning now to the Figures, FIG. 1 shows a workstation 100 equipped with a miniature gas analyzer 102, according to an embodiment of the present disclosure. The workstation 100 represents an indoor fixture such as a desktop computer, a laptop computer, a kiosk, a wall-mounted display, or the like. The workstation 100 includes a display 104 that presents air quality data in the form of a statistical summary 106 and a trend chart 108. The air quality data is sensed locally by the miniature gas analyzer 102 and is then analyzed by electronic components for presentation on the display 104. The electronic components that process and analyze the air quality data may be located within the workstation 100, or at a remote location communicatively coupled to the workstation 100 by a wired or wireless connection, e.g., a network connection. The miniature gas analyzer 102 may be a fixed component of the workstation 100, or the miniature gas analyzer 102 may be a mobile unit that is removably attached to the workstation 100. In one embodiment, the miniature gas analyzer 102 may be part of a smart phone, a tablet computer, a laptop computer, a watch, a pendant, an article of clothing, or another type of mobile unit associated with a user of the workstation 100, wherein the miniature gas analyzer 102 is communicatively coupled to the workstation 100 only while a particular user is working at the workstation 100. The miniature gas analyzer 102 may maintain a user history of locations and associated air quality data to monitor the user's exposure to certain air pollutants. Alternatively, the miniature gas analyzer 102 may maintain a history of air quality data specific to a fixed location of the workstation 100.

In one embodiment, a statistical summary 106 presented on the display 104 includes a humidity reading, a temperature reading, a VOC gas concentration reading, a location, a time stamp, and an overall office air quality index. The statistical summary 106 is exemplary and may include more or fewer data items than are shown in FIG. 1. One or more of the data items may be displayed as a time series graph on the trend chart 108 that occupies a portion of the display 104 so that a user of the workstation 100 can be informed of local air quality in real time. The trend chart 108 may display time trends of individual data items in succession, on a rotating basis. Alternatively, a plurality of time trends may be displayed simultaneously on the trend chart 108. The trend chart 108 may be configurable by the user or by a system administrator.

Figure 2:
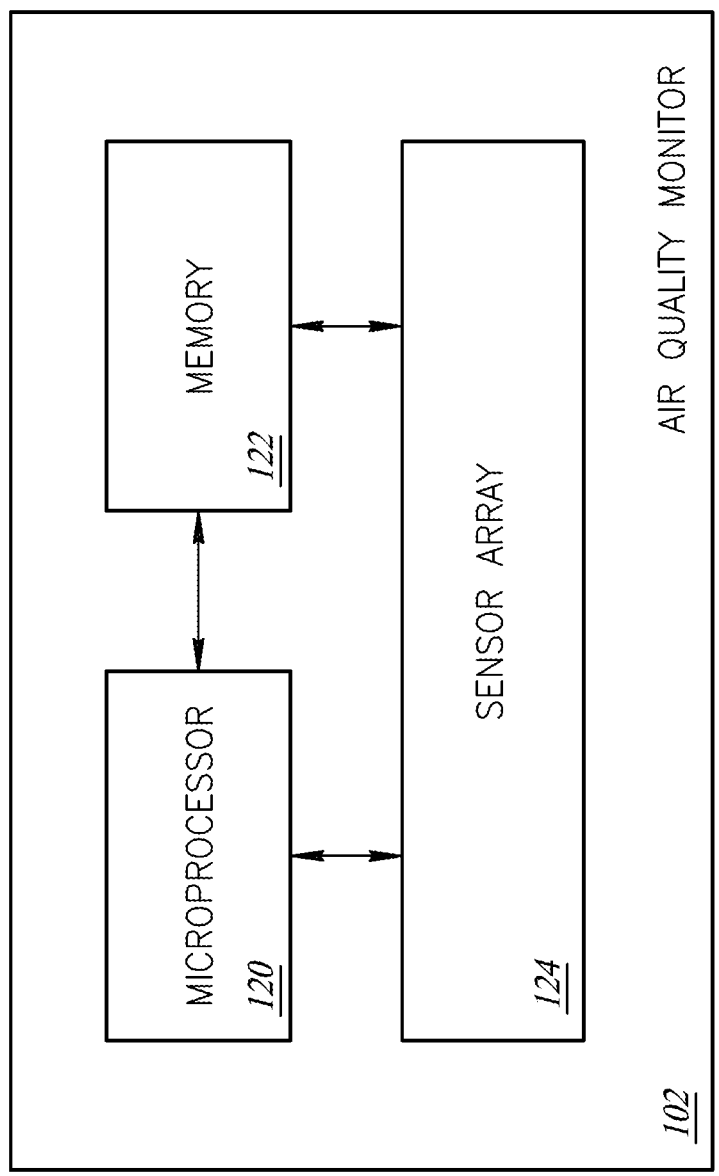
FIG. 2 is a block diagram of the microelectronic gas analyzer shown in FIG. 1, according to an embodiment as described herein.

FIG. 2 shows components of the miniature gas analyzer 102, according to an embodiment of the present disclosure. The miniature gas analyzer 102 is a microelectronic device that includes at least a microprocessor 120, an electronic memory 122, and a micro-sensor array 124. The microprocessor 120 is communicatively coupled to the electronic memory 122 and the micro-sensor array 124. The electronic memory 122 is configured to store instructions for execution by the microprocessor 120 and to store data received from the micro-sensor array 124. The micro-sensor array 124 may also be coupled directly to the electronic memory 122. Any one of the communication paths among components of the miniature gas analyzer 102 may support wired or wireless data communication. The micro-sensor array 124 may be implemented as an application-specific integrated circuit (ASIC) chip. A conventional analog-to-digital converter (ADC) may also be implemented on board the ASIC chip. A portion or all of the electronic memory 122 may be implemented on board the ASIC chip. Furthermore, all components of the air quality monitor may be co-integrated as a system-on-chip (SOC).

The micro-sensor array 124 includes one or more gas sensors, which may include a VOC gas sensor or a plurality of VOC gas sensors, as well as other environmental sensors such as, for example, a pressure sensor, a humidity sensor, a temperature sensor, a flow sensor, and the like. The environmental sensors that sense ambient humidity and temperature may be used to calibrate readings of one or more of the gas sensors according to calibration instructions stored in the electronic memory 122 and executed by the microprocessor 120.

The environmental sensors may be implemented as described in related patent documents by the same inventor as the present patent application, including U.S. Pat. No. 9,176,089, entitled "Integrated Multi-sensor Module," and U.S. Patent Publication No. 2014/0294046, entitled "Microelectronic Environmental Sensing Module," both of which are herein incorporated by reference in their entireties. Alternatively, the environmental sensors may be implemented as described herein, or with some features described in the related patent documents and other features as described herein.

The gas sensor portion of the micro-sensor array 124 may be implemented as described in a related patent document entitled, "Integrated SMO Gas Sensor Module," [U.S. patent application Ser. No. 14/334,572 to Shankar et al., published as U.S. Patent Publication No. 2016/0018356, hereinafter "Shankar"], which is assigned to the same entity as the present patent application, and is herein incorporated by reference in its entirety. Alternatively, the gas sensor portion of the micro-sensor array 124 may be implemented as described in U.S. patent application Ser. No. 15/213,100 issued as U.S. Pat. No. 10,254,261 entitled, "Integrated Air Quality Sensor," which is assigned to the same entity as the present patent application, and is summarized herein and incorporated by reference in its entirety, which implementation has some features that differ from those of Shankar. Alternatively, the gas sensor portion of the micro-sensor array 124 may be implemented so as to combine certain features of Shankar's gas sensors with certain other features of LeNeel's gas sensors. In one embodiment, the entire air quality monitor 102 is on a single substrate 222. In other embodiments, the micro-sensor array 124 is on its own silicon substrate and the microprocessor 120 and the electronic memory 122 are together on a single silicon substrate.

Figure 3A:
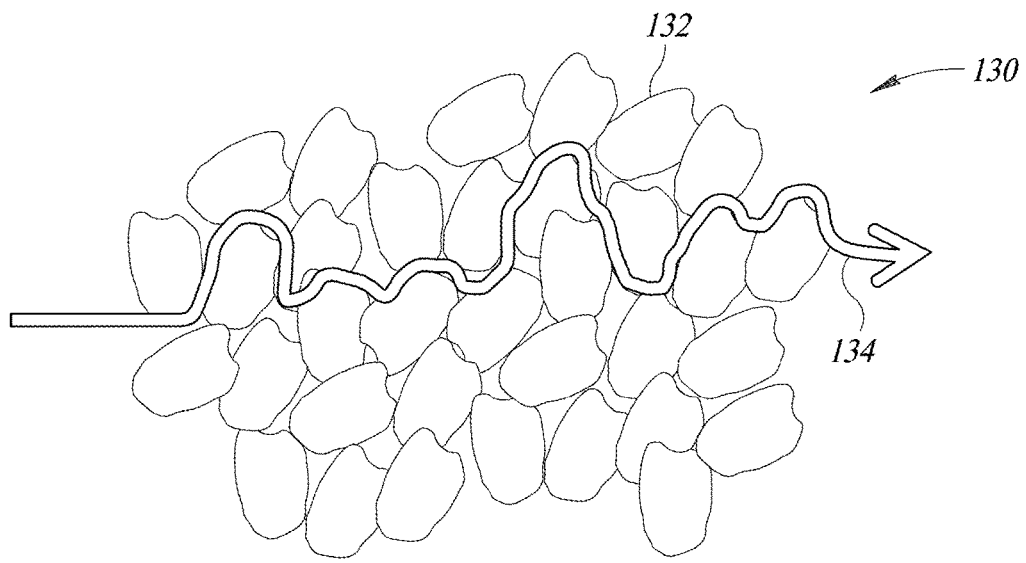
FIG. 3A is a pictorial view of a thick sensor material in powder form that is structured to sustain a bulk chemical reaction, according to the prior art.
Figure 3B:
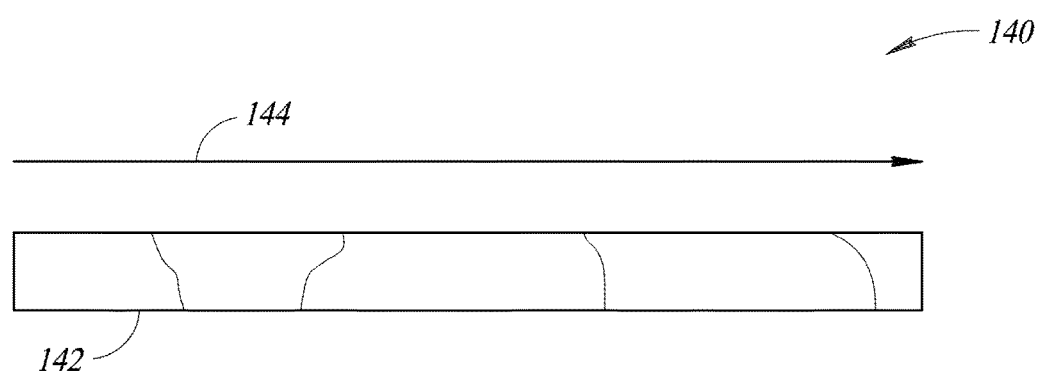
FIG. 3B is a pictorial view of a sensor material in the form of a thin film that is structured to sustain a surface chemical reaction, according to an embodiment as described herein.

FIGS. 3A, 3B contrast the prior art with the present invention for providing an air quality sensor. FIG. 3A shows a bulk sensor material 130, known in the art. The bulk sensor material 130 is in the form of a powder that is structured to sustain a chemical reaction with ambient air. The bulk sensor material 130 is made up of particles 132 that may include multi-crystalline grains of a reactive material. Ambient gas can flow through bulk sensor material, for example, along a circuitous path 134, which facilitates contact between the ambient gas molecules and surfaces of the particles 132. The bulk sensor material 130 may be, for example, tin oxide ($SnO_2$) having a thickness in the range of about 5 μm-20 μm. The bulk sensor material 130 is typically sintered at a temperature of 600 C. The bulk sensor material 130 is a known system and will therefore not be further described. It is large and bulky, and does not fit on a silicon substrate.

FIG. 3B shows a thin film gas sensing material 140, suitable for use in the micro-sensor array 124, according to an embodiment of the present disclosure. The thin film gas sensing material 140 has a structure that supports surface conduction of ambient gas along a substantially straight path 144, and a surface reaction between the ambient gas and a dense, multi-crystalline thin film 142 that is made of a thin film gas sensing material 140. In one example, the thin film 142 is a tin oxide ($SnO_2$) film of thickness 100 nm, about 100 times thinner than the bulk sensor material 130. Other VOC gas sensing materials that can be used as the thin film 142 include zinc oxide ($ZnO_2$) and indium oxide ($In_2O_3$). The thin film 142 may be formed by sputter deposition, followed by sintering at a low temperature of 400 C. The resulting thin film 142 is so dense that it is classified as a ceramic as opposed to a powder. Part or all of the thin film 142 may then be capped with a thin coating of platinum (Pt). The sensitivity of thin film gas sensing materials 140 to various gases that may be present in ambient air is known to change as a function of temperature. The platinum coating may assist in transferring heat to the thin film 142.

Figure 4:
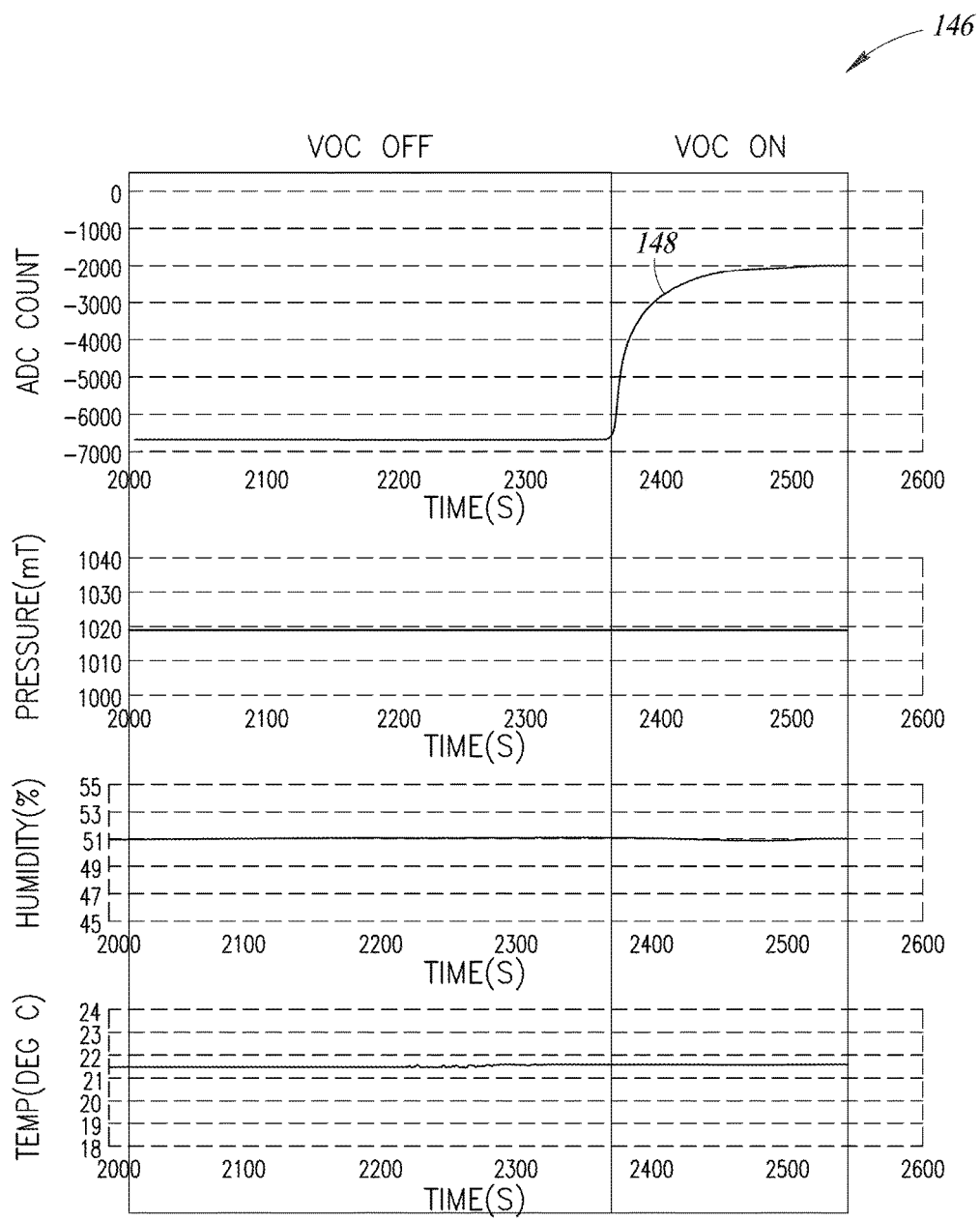
FIG. 4 is a series of graphs of concurrent test measurements of temperature, relative humidity, pressure, and VOCs of ambient air in a test chamber.

FIG. 4 is a series of output plots 146 showing exemplary real-time trends of air quality data detected by the miniature gas analyzer 102. The upper time trend labeled "ADC count" shows the output of an A-to-D converter associated with VOC gas sensor measurements as detected by the micro-sensor array 124. At about 2360 seconds, the VOC sensor registers the presence of a VOC gas as indicated by the rising ADC count value 148. Meanwhile, output values indicating concurrent measurements of the other environmental sensors, pressure, humidity, and temperature, remain constant, for example, at 1020 mT, 51%, and 21.5 C, respectively, while the VOC sensor reacts. The concurrent measurements can be used by the microprocessor 120 to calibrate the VOC gas sensors.

FIG. 5A shows a circuit schematic of the micro-sensor array 124, according to an embodiment of the present disclosure. A single element 150 of the micro-sensor array 124 includes a local temperature sensor 152, a resistive heater 154, and a gas sensor 156 that are formed together on a common substrate. The resistive heater 154 is electronically controlled by the microprocessor 120 according to programmed instructions, so as to tune the gas sensor 156 to be sensitive to a particular gas. The local temperature sensor 152 can be used as a feedback control device for automatically adjusting the resistive heater 154. Power is delivered to the resistive heater 154 via a heater signal line that is driven at a voltage $V_h$ and carries a current $I_h$. The gas sensor 156 includes the thin film 142 made of the thin film gas sensing material 140 shown in FIG. 3B. A temperature of the gas sensor 156 is determined by the voltage $V_h$ and a resistance $R_H$ of an associated resistive heater 154. The element 150 of the micro-sensor array 124 can be operated within a selected temperature range by selecting a particular gas sensing material 140 and then controlling the resistance $R_H$ of the resistive heater 154 to tune the thin film 142 to the desired sensitivity. For example, the element 150 of the micro-sensor array 124 may include tin oxide ($SnO_2$) as an active sensing material and may be operated within a temperature range of 400 C-500 C to detect methane, or within a temperature range of 300 C-350 C to detect carbon monoxide. In one embodiment, the local temperature sensor 152 is configured as a Wheatstone bridge that includes three fixed resistors R1, R2, and R3. To control dissipation of heat and power consumption, heating of the gas sensor 156 is done in a confined manner as explained below.

FIG. 5B shows a schematic of a relative humidity sensor 160 configured as a parallel combination of a variable capacitor $C_{rh}$ and a reference capacitor $C_o$. FIG. 5C shows a schematic of a temperature sensor 162 that includes four resistors, $R_6$, $R_7$, $R_8$, $R_9$ in a Wheatstone bridge arrangement. The temperature sensor 162 will measure a temperature of the ambient environment, in contrast to the local temperature sensor 152 that measures an internal heater temperature for adjusting operation of the VOC gas sensor.

Figure 6:
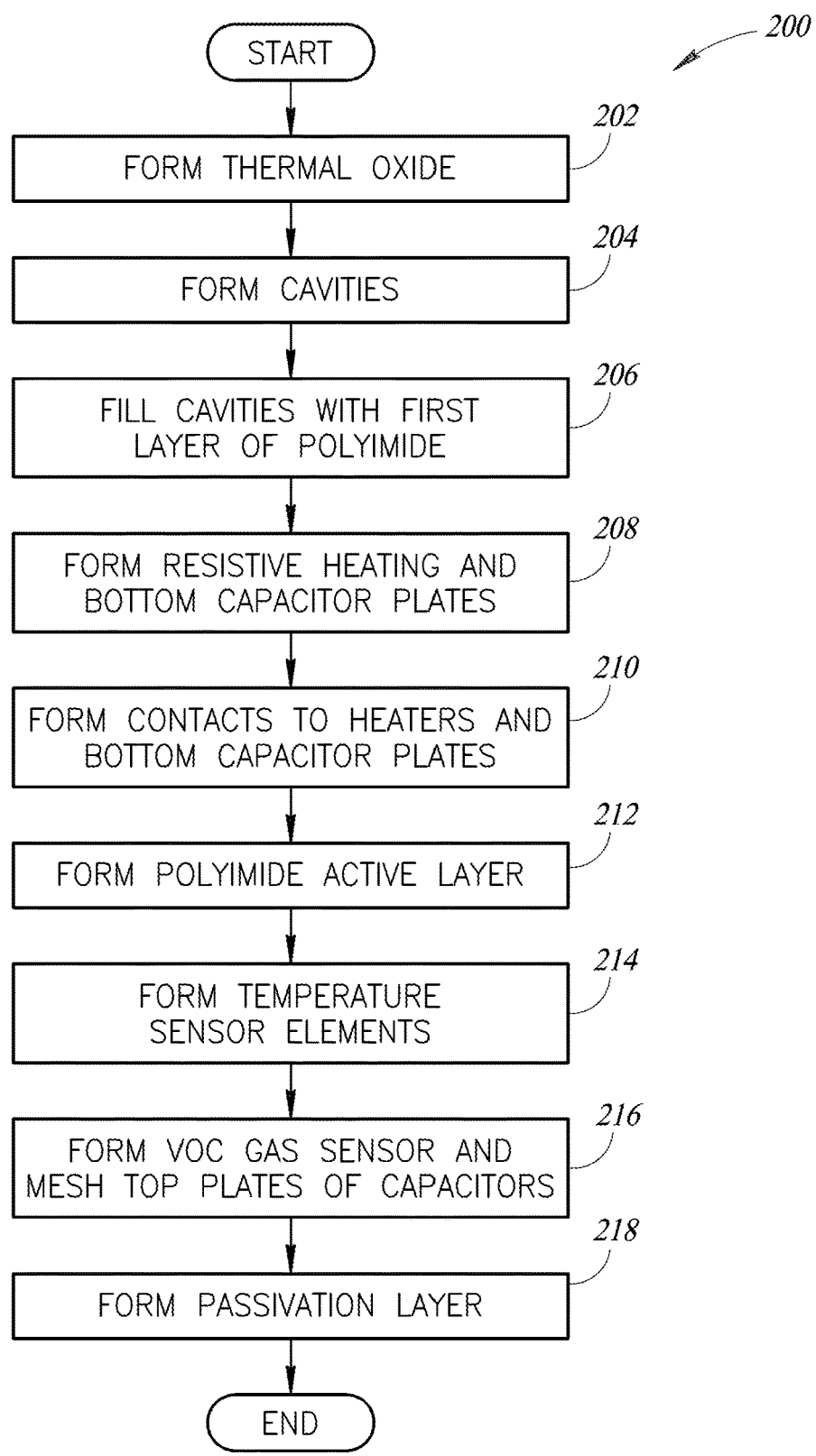
FIG. 6 is a flow diagram showing steps in a method of fabricating sensors of a miniature gas analyzer according to an embodiment as described herein.

FIG. 6 is a flow diagram showing a sequence of steps in a method 200 of fabricating a VOC gas sensor and environmental sensors in the sensor array 124 of the miniature gas analyzer 102, according to an embodiment of the present disclosure. All of the steps in the method 200 following the initial thermal oxide growth can be carried out at temperatures at or below 400 C. Some of the processing steps form dual-purpose films that are patterned in the VOC sensor area so as to perform a first function, and are patterned differently in the humidity sensor area, for example, so as to perform a second function.

With reference to FIGS. 7-9B, the gas sensor 156, suitable for detecting VOCs, is formed adjacent to the resistive heater 154, the local temperature sensor 152, the relative humidity sensor 160, and the ambient temperature sensor 162, as follows:

At 202, a thick oxide 224 is formed on a substrate 222 using, for example, a conventional thermal growth process. The substrate 222 may be, for example, a silicon substrate or a glass substrate having a thickness in the range of about 500 µm-600 µm. The thick oxide 224 has a thickness in the range of about 3 µm-10 µm, as shown in FIG. 7.

At 204, a cavity about 2 µm deep are formed in the thick oxide 224 by patterning the thick oxide 224 using conventional photolithography and etching techniques. For example, the thick oxide 224 may be patterned using a photoresist and etched using a wet chemical etchant such as hydrofluoric acid (HF). The cavity may have sloped sides, as shown in FIG. 7.

Figure 7:
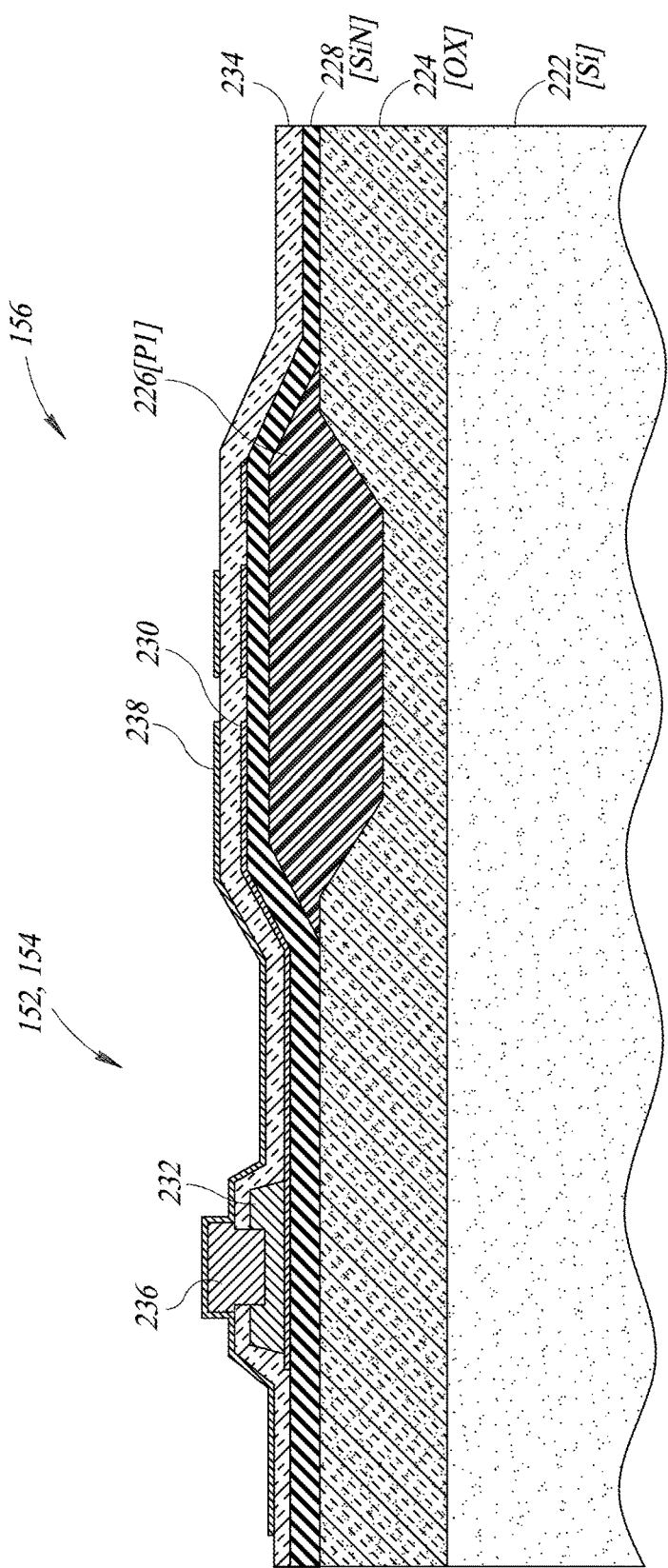
FIGS. 7-9B are cross-sectional views of a sensors at various steps in the fabrication method shown in FIG. 6.

At 206, the cavity is filled with a 4-µm thick first layer of polyimide to form a polyimide well 226 as shown in FIG. 7. The polyimide material can be, for example, a material such as HD8220 available from Fujifilm Corporation of Tokyo, Japan. The polyimide well 226 can be cured at a temperature of 325 C for one hour to reduce the thickness to 3 µm wherein about 2 µm of the polyimide layer is below the surface of the thick oxide 224 and about 1 µm of the polyimide layer is above the surface of the thick oxide 224. Next, a 300 nm thick silicon nitride capping layer 228 (e.g., $Si_3N_4$) is formed on top of the polyimide well 226 using a conventional method of conformal thin film deposition.

Figure 8A:
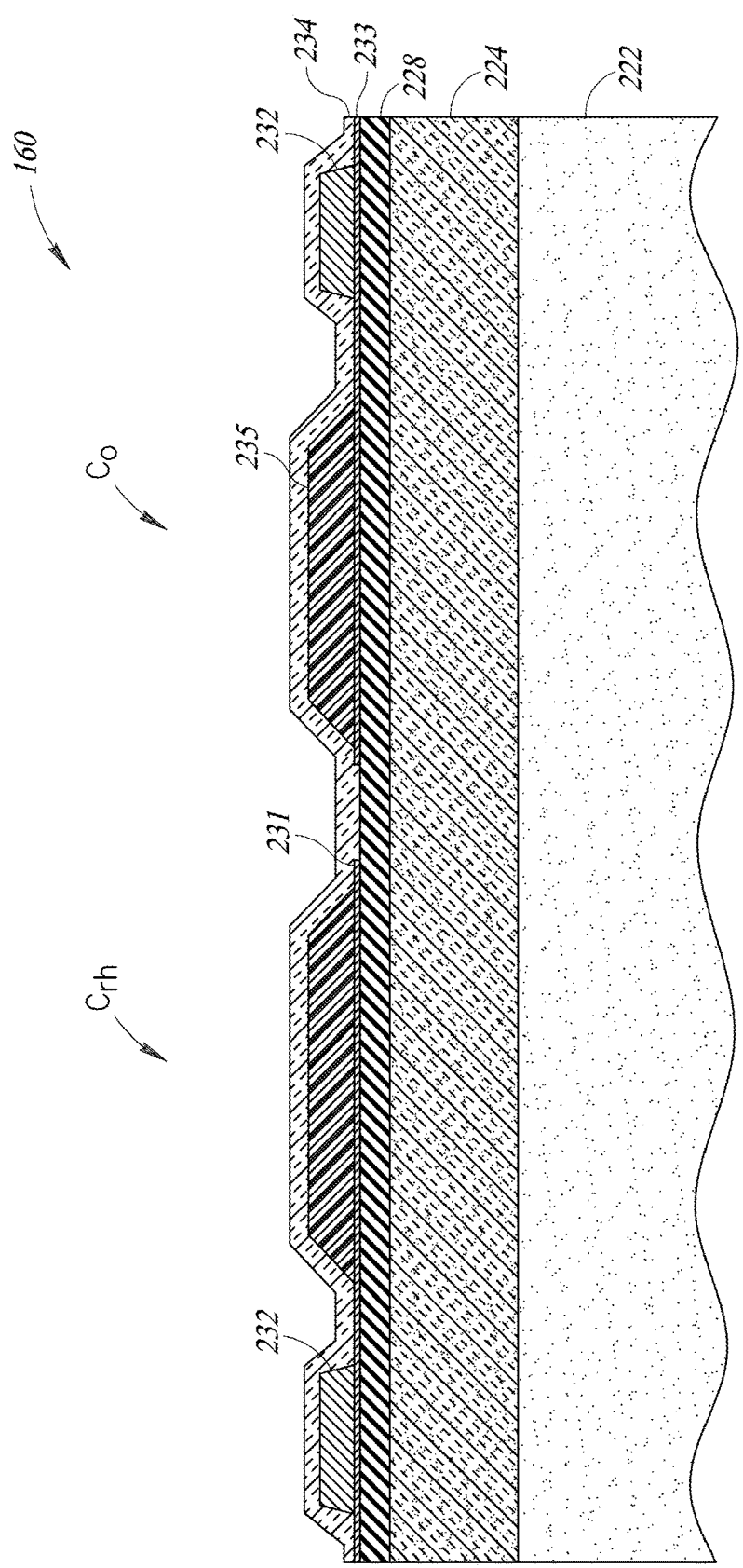

At 208, the resistive heater 154 and a bottom plate of the capacitive relative humidity sensor 160 are both formed from a common 150 nm thick metal layer made of tantalum aluminum (TaAl), according to one embodiment of the present disclosure as shown in FIG. 8A. TaAl features a low thermal coefficient (TCR) that results in a stable resistance. The TaAl metal layer is therefore a multi-use film—a first portion of the TaAl layer serves as a heating element 230 of the resistive heater 154, while a second portion of the TaAl layer serves as a bottom plate 231 of the capacitor $C_{rh}$, and a third portion of the TaAl layer serves as a bottom plate 233 of the reference capacitor $C_o$.

At 210, A first metal layer is then formed on top of the TaAl layer and patterned to form contacts 232 to the heating elements 230 and to the bottom plates 231, 233, as shown in FIG. 8A. The contacts 232 can be made of any metal suitable for use as integrated circuit interconnects such as, for example, aluminum copper (AlCu) having a thickness of about 500 nm. The contacts 232 may have sloped sides.

Figure 8B:
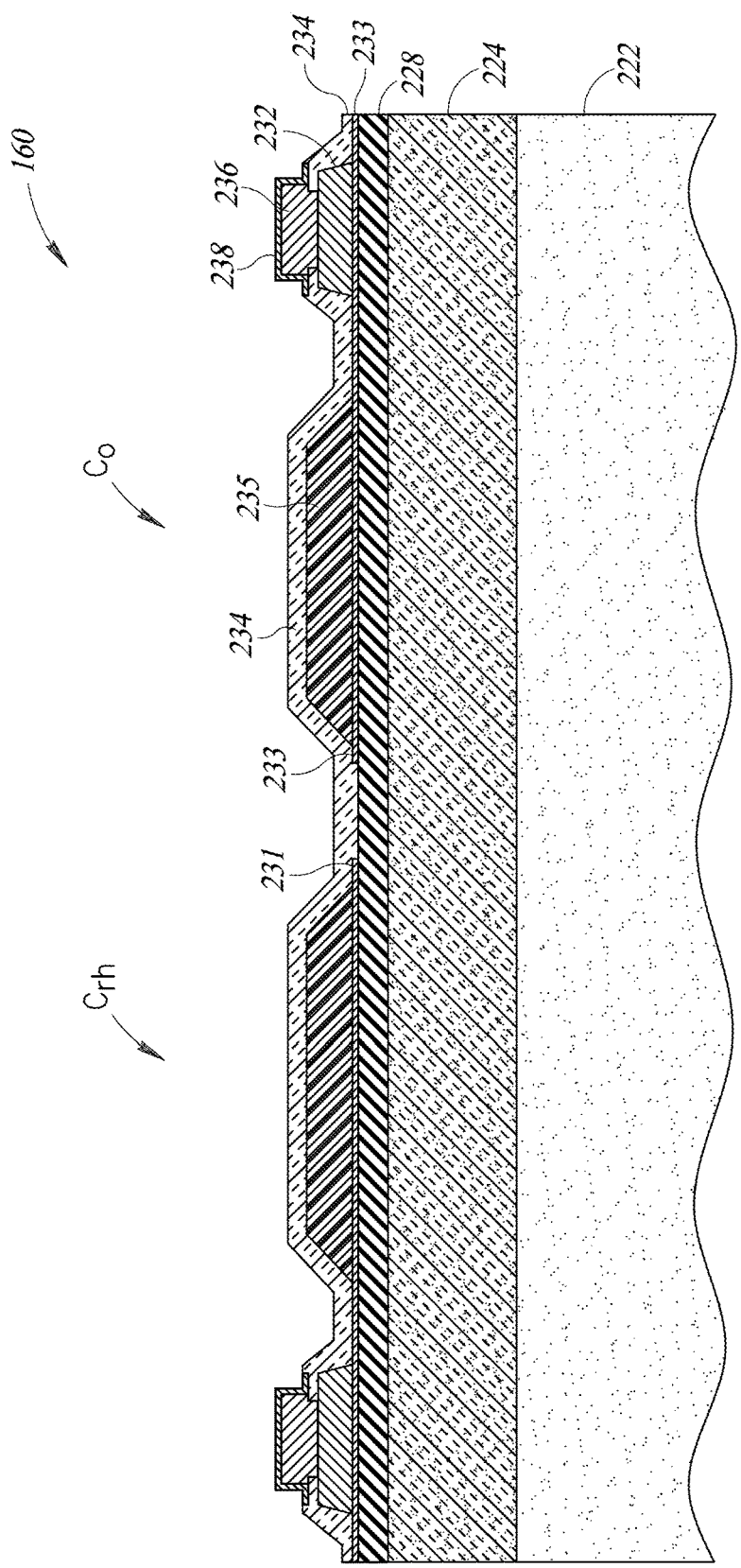

At 212, a second polyimide layer is formed and patterned so as to create active polyimide structures 235 among the metal contacts 232. The active polyimide structures 235 will serve as dielectrics of the parallel plate capacitors $C_{rh}$ and $C_o$. The active polyimide structures 235 may have thicknesses in the range of about 6.0 µm-8.0 µm and may be made of a commercially available polyimide material that is sensitive to humidity. The contacts 232, the TaAl layer, and the active polyimide structures 235 then are covered with a first conformal interlayer dielectric (ILD) 234, e.g., another 300 nm thick layer of $Si_3N_4$. Vias 236 are then etched through the conformal dielectric layer 234 and filled with a second metal layer made of AlCu having a thickness of 500 nm, as shown in FIG. 8B.

Figure 9A:
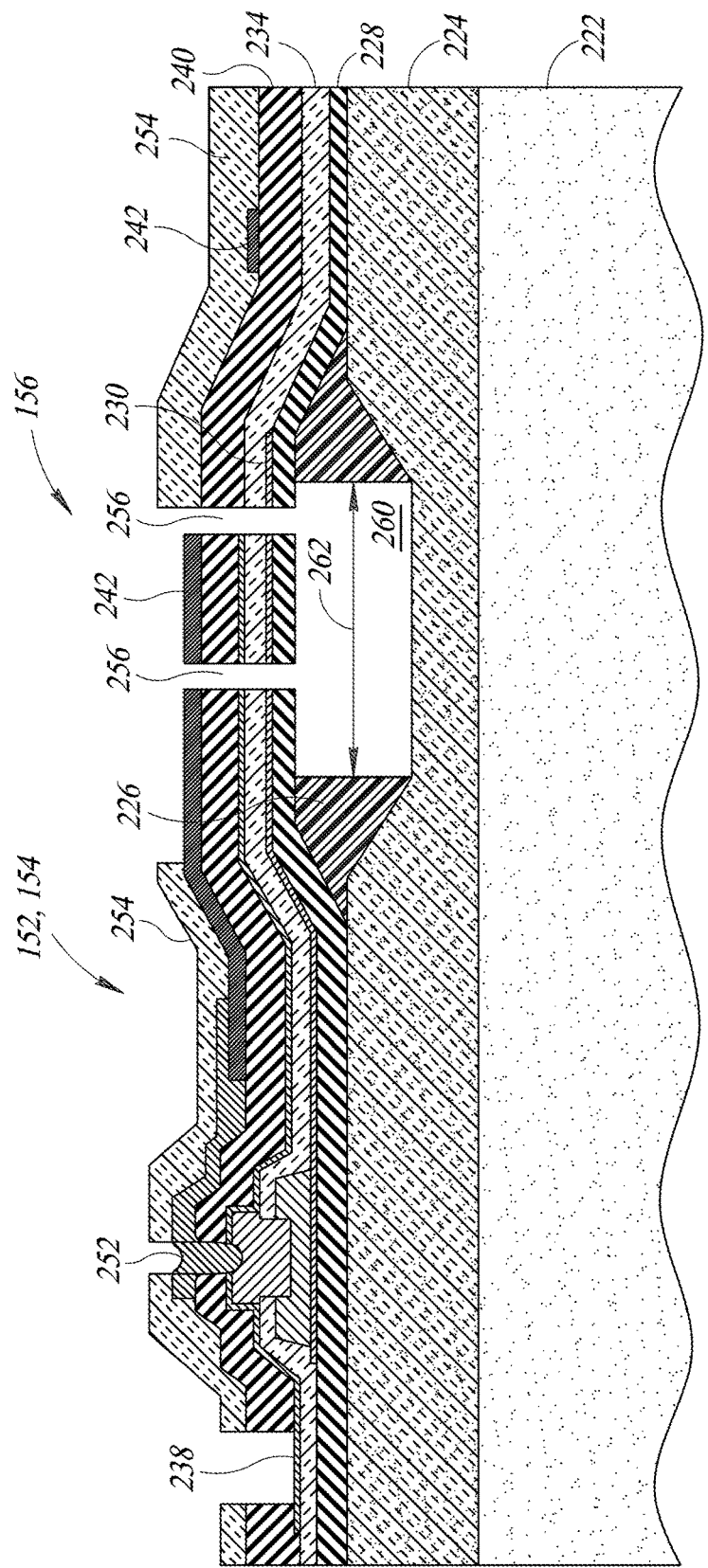
Figure 9B:
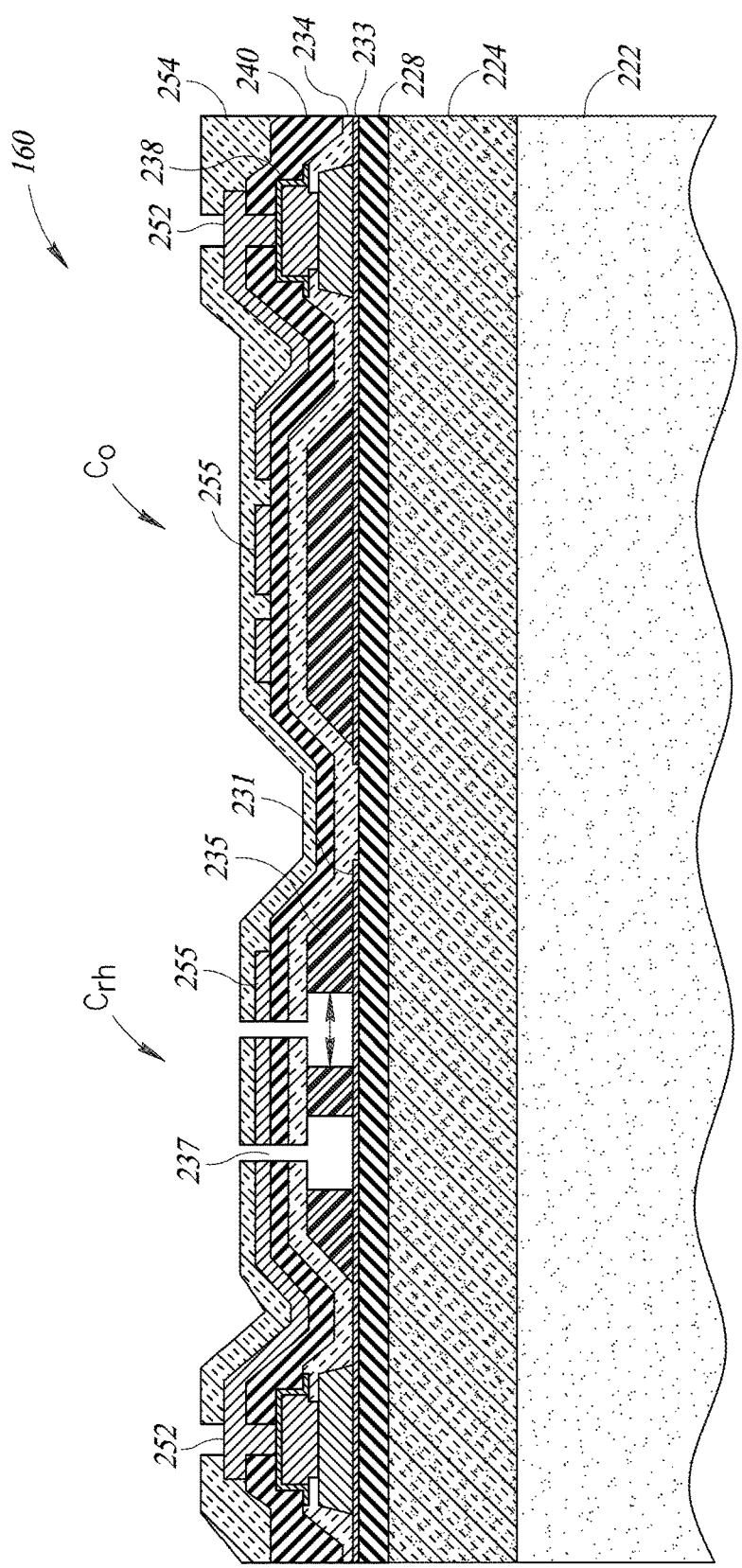

At 214, temperature sensing elements 238 are formed by conformally depositing and patterning a high-TCR thin film over the second metal layer. In the vicinity of the VOC sensor, the patterned high-TCR film functions as a temperature sensor, while in the vicinity of the relative humidity sensor 160, the patterned high-TCR film forms a metal cap over the vias 236 and contacts 232 as shown in FIG. 8B. The temperature sensing elements 238 can be made of, for example, platinum (Pt) or chromium silicide ($CrSi_2$) having a thickness of about 20 nm. A second conformal ILD 240 is then deposited over the temperature sensing elements 238 as shown in FIGS. 9A and 9B. The second conformal ILD 240 can be, for example, 30 nm of $Si_3N_4$. In some embodiments, the temperature sensing elements 238 are optional and may be omitted, depending on a desired level of calibration and accuracy.

At 216, a VOC gas sensor 242 is formed over a polyimide well 226, adjacent to a resistive heater 154, as shown in FIG. 9A. The VOC gas sensor 242 may be made of tin oxide ($SnO_2$) having a thickness in the range of about 30 nm-100 nm. Alternatively, the VOC gas sensor 242 may be made of zinc oxide ($ZnO_2$) having a thickness of about 100 nm, or indium oxide ($In_3O_3$) having a thickness of about 150 nm. Vias 252 are formed in the second conformal ILD 240 and are filled with a third metal layer made of TiW and AlCu having a thickness of about 500 nm. The third metal layer may overlap a portion of the VOC gas sensor film that is outside the vicinity of the polyimide well 226, as shown in FIG. 9A. Where the third metal layer is situated over an active polyimide structure 234, the third metal layer is patterned to form a metal mesh top capacitor plate 255.

At 218, a passivation layer 254 is formed over the metal mesh top capacitor plates 255 and the VOC sensor 242, as shown in FIGS. 9A, 9B. The passivation layer 254 may be made of SiN. The passivation layer 254 is patterned to expose the VOC sensor 242, and to provide a signal path via the various metal layers to access the temperature sensor 238 and the contact 232 to the heating element 230. The VOC sensor 242 has an exposed active sensing area of about 200 $\mu m^2 \times 100$ $\mu m^2$. Openings 237 are etched through the passivation layer 254, through holes in the metal mesh top capacitor plate 255, and through the various ILD layers below the metal mesh top plate of $C_{rh}$ to expose the active polyimide to ambient air. Additional lateral removal of a plurality of polyimide plugs having widths 239 increases the surface area of polyimide that contacts the ambient air. Polyimide removal may utilize a dry etch or a wet etch chemistry suitable for removing photoresist. When the humidity of the ambient air changes, the dielectric constant, κ, of the active polyimide structure will be affected, and will cause variation in the capacitance of $C_{rh}$ relative to the reference capacitor $C_o$. A completed relative humidity sensor 160 is shown in cross-section in FIG. 9B.

Meanwhile, during the same processing step, polyimide material is removed from the polyimide wells 226. Openings 256 are formed by etching through the VOC sensor 242 and the ILD layer stack to expose the polyimide wells 226. The additional lateral etching step removes polyimide material from the polyimide wells 226, leaving air pockets 260 underneath the heating elements 230. The air pockets 260 have widths 262. The widths 262 of the air pockets are desirably much larger than the openings 256 so that air is effectively trapped within the air pockets 260, while being maintained at an atmospheric pressure of the ambient air. A curing step can then be performed at 400 C for two hours at atmospheric pressure to shrink and harden polyimide material remaining in the polyimide wells 226, thereby solidifying the walls of the air pockets 260. The air pockets 260 provide thermal insulation to trap heat produced by the heating elements 230 so that the heat is spatially confined within a local vicinity of the adjacent VOC sensor and is not transmitted to other VOC sensors in the micro-sensor array 124.

Figure 10:
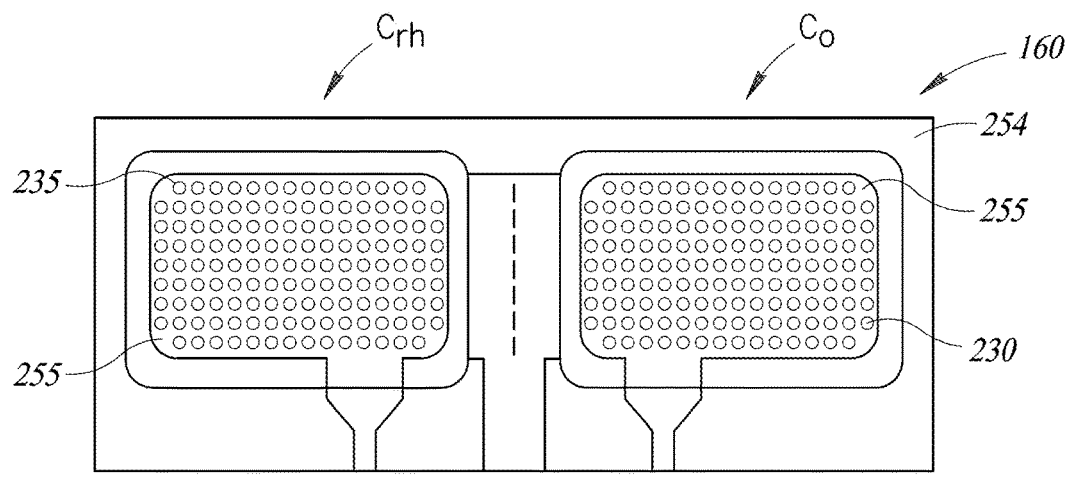
FIG. 10 is a top plan view of a completed miniature relative humidity sensor, according to one embodiment as described herein.

FIG. 10 shows a top plan view of the relative humidity sensor 160, in which the metal mesh top plate 255 of $C_{rh}$ is on the left and the metal mesh top plate of the reference capacitor $C_o$ is on the right. Each parallel plate capacitor in the relative humidity sensor 160 has a surface area of about 200×300 microns. The top plate and bottom plate overlap area is about 11.2E-8 $m^2$. The dielectric constant of the active polyimide material is about κ=3. The capacitance of the relative humidity sensor therefore can be estimated as:

$C = \varepsilon A/d$ $= (3\varepsilon_o F/m)(11.2\text{E-8 } m^2/(7.0\text{E-6 m}))$ $= 0.425$ pF.

Figure 11:
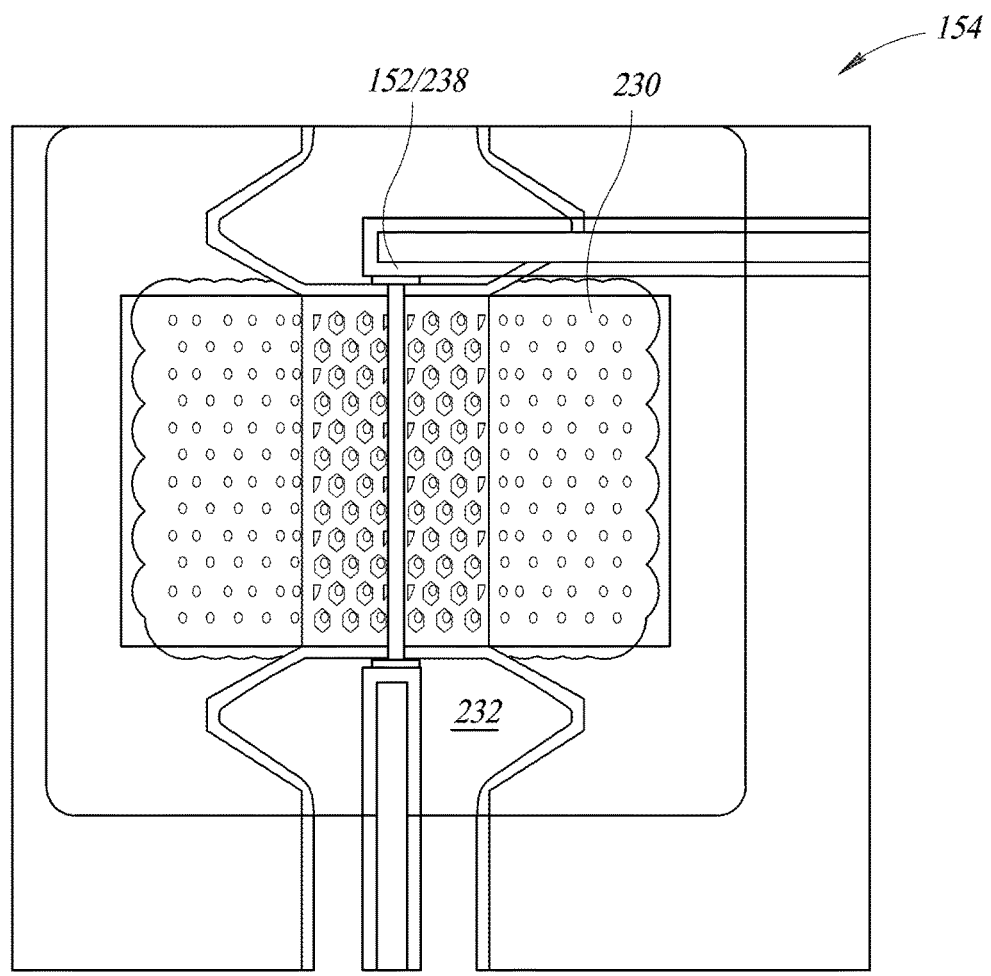
FIG. 11 is a top plan view of a completed miniature VOC sensor, according to one embodiment as described herein.

FIG. 11 shows a top plan view of an exemplary temperature sensor 152 and an exemplary resistive heater 154, according to an embodiment of the present disclosure. The resistive heater 154 can be designed as a metal mesh heating element 230 in which the openings 256 lead to the air pockets 260 located below the heating element 230. The contact 232 provides electrical power to the heating element 230. The temperature sensor 152 is disposed in a layer above the heating element 230, and extends to a position directly below the VOC sensor.

Figure 12:
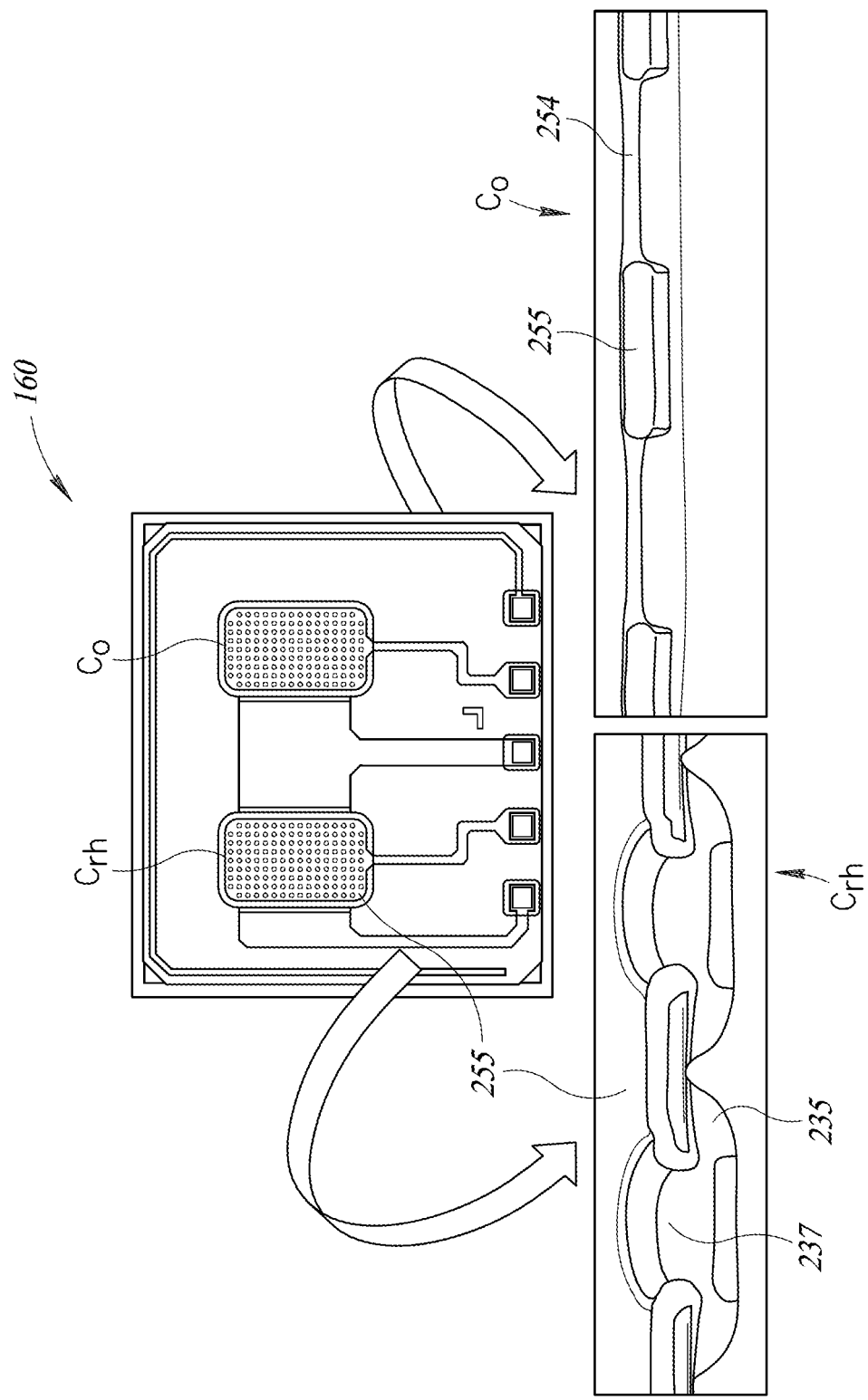
FIG. 12 includes a top plan view and cross-sectional views of a relative humidity sensing capacitor and a reference capacitor in an electronic package that includes wiring and contact pads, according to one embodiment as described herein.

FIG. 12 shows a top plan view of the relative humidity sensor 160, along with cross-sectional scanning electron micrographs (SEMs) of the metal mesh top plates 255 of $C_{rh}$ (left) and the reference capacitor $C_o$ (right). The openings 237 exposing the active polyimide structures 235 to ambient air are evident in the left hand image, while no such openings are evident in the right hand image.

By fabricating the temperature sensor 152, the resistive heater 154, one or more VOC sensors 156, the relative humidity sensor 160, and the ambient temperature sensor 162 using the same processing steps as outlined above, it is possible to co-integrate all five sensor functions on the same die, creating a full gas analyzer.

All of the U.S. patents, U.S. patent application publications, U.S. patent applications, foreign patents, foreign patent applications and non-patent publications referred to in this specification and/or listed in the Application Data Sheet are incorporated herein by reference, in their entireties.

It will be appreciated that, although specific embodiments of the present disclosure are described herein for purposes of illustration, various modifications may be made without departing from the spirit and scope of the present disclosure. The various embodiments described above can be combined to provide further embodiments. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:
1. A microelectronic gas analyzer, comprising:
a substrate;

a humidity micro-sensor formed on the substrate, the humidity micro-sensor configured to monitor humidity of ambient air, the humidity micro-sensor including capacitors having first and second plates;

a temperature micro-sensor formed on the substrate, the temperature micro-sensor configured to monitor a temperature of the ambient air;

a gas micro-sensor formed on the substrate, the gas micro-sensor configured to detect a particular gas species present in the ambient air, the gas micro-sensor including gas sensitive material;

a dielectric layer extending from the humidity micro-sensor to the gas micro-sensor, the dielectric layer being between the first and second plates of the capacitors and between the substrate and the gas sensitive material;

a microprocessor communicatively coupled to the humidity micro-sensor, the temperature micro-sensor, and the gas micro-sensor; and an electronic memory communicatively coupled to the microprocessor, the electronic memory configured to store instructions for execution by the microprocessor and to store data received from the humidity micro-sensor, the temperature micro-sensor, and the gas micro-sensor.

2. The microelectronic gas analyzer of claim 1 wherein the substrate is a glass substrate.

3. The microelectronic gas analyzer of claim 1 wherein the microprocessor and the electronic memory are shared components within a mobile computing device.

4. The microelectronic gas analyzer of claim 1 wherein the microprocessor and the electronic memory are shared components within a fixed computing device.

5. The microelectronic gas analyzer of claim 1, further comprising:
an air pocket; and
a heating element overlying the air pocket, the dielectric layer being formed on the heating element.

6. The microelectronic gas analyzer of claim 5 wherein the dielectric layer includes a first opening overlying the air pocket, and a second opening overlying the second plates of the capacitors.

7. A device, comprising:
a substrate;
a temperature sensor on the substrate, the temperature sensor configured to sense a temperature of a surrounding environment;
a humidity sensor on the substrate, the humidity sensor configured to sense a humidity of the surrounding environment, the humidity sensor including first and second capacitors each having first and second plates, the first and second capacitors including a dielectric; and
a gas sensor on the substrate, the gas sensor configured to detect a selected gas species in the surrounding environment, the gas sensor including gas sensitive material; and
a passivation layer on the temperature sensor, the humidity sensor, and the gas sensor, the passivation layer including a first opening that exposes the dielectric of the first capacitor to the surrounding environment, and a second opening that exposes the gas sensitive material of the gas sensor to the surrounding environment, wherein the dielectric is between the first and second plates of each of the first and second capacitors and between the substrate and the gas sensitive material.

8. The device of claim 7 wherein the temperature and the humidity are used to calibrate the gas sensor.

9. The device of claim 7 wherein the first and second capacitors include the second plate having a plurality of openings, and the dielectric being a dielectric layer.

10. The device of claim 7 wherein the gas sensitive material includes one or more of $SnO_2$, $ZnO_2$, or $In_2O_3$.

11. The device of claim 7, further comprising a resistive heater having a heating element made of a transition metal having a low temperature coefficient of resistance (TCR).

12. The device of claim 11, wherein the transition metal of the heating element includes one or more of Ta and Al.

13. The device of claim 7 wherein the temperature sensor includes a high TCR metal that includes one or more of Pt or $CrSi_2$.

14. The device of claim 7, further comprising:
a air pocket on the substrate; and
a heating element on the substrate, the air pocket, the heating element, and the gas sensitive material being aligned with each other.

15. A method, comprising:
forming a gas micro-sensor on a substrate; and
forming a resistive heater on the substrate and adjacent to the gas micro-sensor;
forming a local temperature sensor on the substrate and adjacent to the gas micro-sensor, the local temperature sensor configured to sense a temperature of the resistive heater;
forming a relative humidity sensor on the substrate, the relative humidity sensor including a variable capacitor having a dielectric and a reference capacitor having a dielectric; and
forming an ambient temperature sensor on the substrate, the ambient temperature sensor configured to sense a temperature of an ambient environment;
forming a passivation layer on the gas micro-sensor, the resistive heater, the local temperature sensor, the relative humidity sensor, and the ambient temperature sensor;
forming a first opening in the passivation layer, the first opening overlying the variable capacitor such that the dielectric of the variable capacitor is exposed to the ambient environment; and
forming a second opening in the passivation layer, the second opening overlying the gas micro-sensor such that the gas-micro sensor is exposed to the ambient environment.

16. The method of claim 15 wherein the gas micro-sensor includes one or more of zinc oxide ($ZnO_2$), indium oxide ($In_3O_3$), or tin oxide ($SnO_2$).

17. The method of claim 15, further comprising:
forming an air cavity that provides thermal insulation between the substrate and the gas micro-sensor.

18. The method of claim 15 wherein the dielectrics of the variable capacitor and the reference capacitor are made of polyimide.

19. The method of claim 15, further comprising:
removing a portion of the dielectric of the variable capacitor that is between plates of the variable capacitor.

20. The method of claim 15, further comprising:
forming a plurality of holes through a plate of the variable capacitor.

* * * * *